(12) United States Patent
Echner

(10) Patent No.: US 8,565,378 B2
(45) Date of Patent: Oct. 22, 2013

(54) METHOD AND DEVICE FOR DEFINING A BEAM OF HIGH-ENERGY RAYS

(75) Inventor: Gernot Echner, Wiesenbach (DE)

(73) Assignee: Deutsches Krebsforschungszentrum Stiftung des Oeffentlichen Rechts, Heidelberg (DE)

( * ) Notice: Subject to any disclaimer, the term of this patent is extended or adjusted under 35 U.S.C. 154(b) by 386 days.

(21) Appl. No.: 12/662,814

(22) Filed: May 5, 2010

(65) Prior Publication Data

US 2010/0270480 A1    Oct. 28, 2010

Related U.S. Application Data

(63) Continuation-in-part of application No. 11/919,707, filed as application No. PCT/EP2005/008659 on Aug. 10, 2005, now abandoned.

(30) Foreign Application Priority Data

May 6, 2005 (EP) .................................. 05009871

(51) Int. Cl.
  *A61N 5/10* (2006.01)
(52) U.S. Cl.
  USPC ............................................ 378/65; 378/148
(58) Field of Classification Search
  USPC ...................... 378/65, 64, 147, 148, 149, 150
  See application file for complete search history.

(56) References Cited

U.S. PATENT DOCUMENTS

| | | | | |
|---|---|---|---|---|
| 4,450,578 A | * | 5/1984 | Hill ................................ | 378/152 |
| 5,748,703 A | * | 5/1998 | Cosman ......................... | 378/152 |
| 5,991,362 A | * | 11/1999 | Jones ............................. | 378/152 |
| 7,132,674 B2 | | 11/2006 | Pastyr | |
| 2009/0220046 A1 | * | 9/2009 | Ji et al. ............................ | 378/65 |

FOREIGN PATENT DOCUMENTS

| | | |
|---|---|---|
| EP | 1 454 653 | 9/2004 |
| JP | 04072880 | 3/1992 |
| JP | 07047142 | 2/1995 |
| JP | 2004267250 | 9/2004 |

* cited by examiner

*Primary Examiner* — Hoon Song
(74) *Attorney, Agent, or Firm* — Paul Vincent

(57) ABSTRACT

The invention relates to a method and device for operating collimator (1) for limiting a beam of high-energy radiation (2) which, starting from an essentially point-shaped radiation source (3), is directed onto an object (4) to be treated and which is used especially for stereotactic, conformal radiation therapy of tumors, wherein the collimator (1) has an iris diaphragm (5) as a beam-limiting means. For such a collimator (1), a high degree of shielding for minimal overall height and with a variable opening size of the diaphragm opening (12) is achieved, in that the iris diaphragm (5) has at least three diaphragm leaves (6, 6', 6", or 7, 7', 7", 7"', or 8, 8', 8", 8"', 8"", or 9, 9', 9", 9"', 9"", 9""') which have touching side surfaces (10) enclosing the same angle ($\alpha$), wherein the diaphragm leaves (6, 6', 6", or 7, 7', 7", 7"', or 8, 8', 8", 8"', 8"", or 9, 9', 9", 9"', 9"", 9""') open up a beam-limiting opening (12) such that a sliding movement (13) along the side surfaces (10) takes place by a number of diaphragm leaves (6, 6', 6", or 7, 7', 7", 7"', or 8, 8', 8", 8"', 8"", or 9, 9', 9", 9"', 9"", 9""') which is reduced by at most one.

32 Claims, 12 Drawing Sheets

METHOD AND DEVICE FOR DEFINING A BEAM OF HIGH-ENERGY RAYS

This application is a continuation in part of Ser. No. 11/919,707 filed on Oct. 31, 2007 now abandoned as a 371 of PCT/EP2005/008659 filed Aug. 10, 2005 and claiming Paris Convention priority to EP 05009871.4 filed May 6, 2005 the entire disclosures of which are hereby incorporated by reference

BACKGROUND OF THE INVENTION

The invention relates to a method and device having a collimator for limiting a beam of high-energy radiation directed from an essentially point-shaped radiation source onto an object to be treated for stereotactic, conformal radiation therapy of tumors, wherein the collimator has a scanning device with a collimator and a drive mechanism for scanning an area of an object being treated with a beam of rays defined by the collimator.

Collimators for limiting a beam of high-energy radiation are used for diagnostic purposes and for the treatment, in particular, of tumors. Here, the collimators are used to limit the beam, so that healthy tissue lying next to the diagnostic or treatment area is protected as much as possible from the radiation in order to prevent injury or to reduce it to a minimum.

Collimators were originally designed to delimit only the size of an irradiation field. If only X-rays were used for imaging, the patient was not seriously impaired. Only therapeutic irradiation with high-energy rays, e.g. to destroy tumorous tissue, damaged healthy tissue in the excessively irradiated areas, i.e. outside of the ill tissue to be irradiated. These excessively irradiated areas were generated since the contour of the ill tissue was not simulated by the collimators and also since half shadows were generated at the boundaries of the irradiated area, where, in particular with large irradiation fields, the entire strength of the shielding material was not available, since it was not oriented parallel to the rays.

One example of such a collimator of older design is shown in U.S. Pat. No. 2,675,486. This document concerns a collimator for limiting high-energy rays, comprising four ray-delimiting blocks, which can be displaced in one plane using bordering side surfaces, such that a square ray limitation of different sizes can be set. Since tumors tend to have a round rather than square shape, there are large excessively irradiated corner areas. With large irradiation fields, one moreover obtained large half shadow areas, since the block limits no longer extend parallel to the divergent path of rays.

For this reason, the experts tried to solve these problems:
Departing from a collimator of the above-mentioned type, DE 20 53 089 A1 proposes, for the field of X-ray imaging which is related to the field of the inventive object, providing shielding elements in the form of bordering triangles, in order to obtain an approximately circular irradiation field, which corresponds more to the shape of an irradiation area, such that excess irradiation caused by the corners of the above-mentioned square ray limitation is prevented by approximately 30%. The remaining excess irradiation and half shadow formation do not represent a serious problem, since it only concerns X-rays for imaging and not therapeutic irradiation with rays of substantially higher energy.

DE 15 89 432 A1 proposes a collimator to be used with the relevant, ionizing, high-energy rays which are suited for the treatment of tumors, wherein bordering wedge-shaped irradiation shielding elements can be displaced in one plane such that hexagonal, octagonal or rectangular openings can be combined. This collimator, however, does not sufficiently simulate the tumor shape and provides no suppression of half shadows. For large irradiation fields, wherein the path of rays extends at a great inclination to the limitation of the shielding material, a large half shadow is generated.

DE 10 37 035 B is also based on a collimator of the type of the first-mentioned document, wherein the four ray-limiting blocks are divided into two parts along an inclined line for high-energy therapeutic rays, wherein the line extends to that location where the inner and end surfaces (i.e. the surface bordering the next block) meet. One thereby obtains a main and a side part of each block which can be mutually displaced. This permits formation of different contours, which also reduces excessive irradiation compared to square ray limitation. The problem of simulation of the shape of a tumor or another area to be irradiated is, however, only very insufficiently solved, and the problem of half shadows is not solved at all.

DE 15 64 765 A1 finally solves the problem of half shadows. This document is also based on a collimator of the type disclosed in the first-mentioned document, with four bordering radiation-limiting blocks which can be displaced in a plane. It is based on the object to obtain a field with sharp borders, i.e. a field without half shadows. Towards this end, it is proposed to design and pivotably displace the blocks in such a fashion that the front ends forming the radiation limit are directed onto the radiation source in each setting. The material of the blocks thereby always shields the full radiation. However, this collimator only forms square irradiation fields, such that large excessively irradiated areas on the corners must be accepted.

FR 2 524 690 addresses both the problem of excessively irradiated areas, and the half shadow problem. This document proposes to arrange bordering plates, which can be displaced in a plane, in several planes for preventing or reducing half shadows, in order to obtain a stepped, truncated pyramid-shaped ray-limiting opening. In this fashion, the half shadow is minimized. It only appears in that area where the rays cross the stepped shape. The larger the surface to be limited, the larger becomes this stepped area of the half shadow which still remains despite this measure. A further disadvantage of this approach consists in that only polygons can be formed as irradiation field limitation in dependence on the number of plates, and shaping of the true tumor contour is not possible.

EP 1 367 604 A1 discloses a device for concentrating an X-ray into a micro-X-ray, wherein the concentration is obtained by reflection on reflecting inner surfaces of a capillary tube. This capillary tube is formed by displacing concentrically arranged rod segments, which can be displaced and adjusted by screws. This device only permits very limited point irradiation. Moreover, the effect of reflection on reflecting inner surfaces is not suited for therapeutic rays which are in a megavolt range.

In order to improve the simulation of the tumor shapes and reduce the excessive irradiation to a minimum, one finally started to use changeable fixed collimators. The tumor shape was thereby detected from different spatial directions, and several fixed collimators were produced for each irradiation, which were then used for irradiation from the different directions. This is advantageous due to exact shaping and exact adjustability of the limitations to the path of rays, wherein any half shadow is eliminated. The disadvantage is, however, that the method is complicated, requiring permanent collimator change, which consumes a great deal of time on expensive devices, and is also costly since many collimators must be produced for each irradiation, which are useless after that, since they are determined for use for one patient only and can be used for that patient only within a limited time period, since the shape of the tumor permanently changes due to growth, decrease, or shape changes.

In order to reduce this effort, multileaf collimators were generated, having a plurality of narrow, closely adjacent leafs (i.e. diaphragm leaves), with which the shape of a tumor can be simulated via actuation of the leaves. These multileaf collimators were initially advantageous in that almost any shape could be quickly adjusted, but are disadvantageous in that the mechanism with adjustment means for each leaf is very complex and also since a more or less large half shadow was generated on each limit of the irradiation field by a leaf, in dependence on the separation between the leaf and the axis of the path of rays.

In order to avoid such half shadows, EP 1 153 397 B1 proposes leaves having adjustable front edges, wherein a mechanism always adjusts them parallel to the path of rays. This requires, however, an even more complex mechanism of the multileaf collimator.

In order to avoid this complex mechanism and be more flexible in shaping a surface to irradiated, DE 199 22 656 A1 finally proposes a scanning device with a collimator opening which is sufficiently small that the areas of the object to be irradiated can be irradiated with sufficient accuracy (FIG. 3). In the above-mentioned proposal, a small collimator opening provides great accuracy, but slower scanning. A large diaphragm opening provides faster scanning but not the required accuracy. The use of multi-hole plates for generating a bundle of several scanning rays (FIGS. 5 and 5a) thereby did not reduce the irradiation to a satisfactory degree. The multi-hole plate was fixed relative to the irradiation area, and even smaller diaphragm openings had to be used for exact irradiation of the edge areas, i.e. the plates had to be changed.

In order to increase the scanning speed and still obtain high accuracy, DE 101 57 523 C1 finally proposes a collimator with several collimator openings of different sizes, which can optionally be brought into the path of rays. This was preferably effected using a revolver-like mechanism which rotates a round plate having openings of different sizes. A material thickness of 6 to 10 cm is necessary for shielding the high-energy rays which are used in therapy today. In this fashion, one either obtains a very heavy collimator, or one must make do with a few, e.g. three opening sizes. Even with such a limitation, the openings which are not used must be covered to prevent the generation of regions which are only shielded by an insufficient material thickness. A shielding plate is required in addition to the plate with openings, which must also have a thickness of several centimeters. For this reason, the collimator becomes relatively heavy, which correspondingly increases the requirements for guides and drives. This collimator is also disadvantageous in that, for the above-mentioned reasons, only a few of the fixed collimator openings are available, thereby strongly limiting the variability of ray collimation. In particular, for the above-mentioned reasons, it is not possible to provide large openings of different diameters for initially treating an area of the surface to be irradiated, which is as large as possible in order to subsequently treat the edge areas with stepped finer bundles of rays. Since the dwell time of ray application for each point of a surface is several seconds, the scanning of an area with fixed sizes of ray bundles is more time-consuming than with sizes which can be optimally adjusted. This is the case, in particular, when the ray bundles are narrower than possible with regard to the irradiation area. This increases the overall treatment time. This is not only unpleasant for the patient who must remain stationary, but also reduces the number of treatments that can be performed on one device, which is economically very important in view of the high acquisition and operating costs of such devices. Moreover, the accuracy of edge area detection is limited, which is critical in areas such as bordering nerves.

EP 0 382 560 A1 discloses an iris diaphragm as a ray-limiting means, and mentions irradiation by "scanning". It does not concern a scanning motion of the type mentioned in DE 199 22 656 A1, wherein rays are applied onto a surface through the scanning motion of a limited ray, wherein these applications are sequentially performed from different spatial angles by displacing a gantry with radiation source, ray limitation and scanning device about the patient. In EP 0 382 560 A1, the above-mentioned circling of the area to be irradiated is called "scanning". The application from a direction is not effected by scanning of an area, i.e. "scanning" as usually understood in technology. The irradiation to be applied in each case from a direction onto a treatment surface is rather approximately adjusted with the iris diaphragm, as shown in FIGS. 2 through 5, and described in the description of EP 0 382 560 A1. These surfaces are then always polygons in accordance with the diaphragm leaves of the iris diaphragm, i.e. approximately circles. This rough definition of an area cannot simulate the tumor shape and therefore destroys the healthy tissue, which is also irradiated. For this reason, the proposal of EP 0 382 560 A1 has disadvantages which can no longer be accepted today, and have already been overcome by the technical development proposed by DE 199 22 656 A1 and DE 10 157 523 C1.

The invention is therefore based on a scanning device as disclosed in DE 101 57 523 C1. This document corresponds to the collimator mentioned above. The invention is based on the problem of configuring a collimator of the type previously described above and method for use thereof, such that a variable opening size of the diaphragm opening can be achieved with a high degree of shielding and low overall height.

SUMMARY OF THE INVENTION

The problem is solved according to the invention with a method for stereotactic, conformal radiation therapy of tumors, the method comprising the steps of:
  a) positioning an iris diaphragm collimator to irradiate the tumor from a first irradiation angle, the iris diaphragm having at least three diaphragm leaves, wherein the diaphragm leaves open up a beam-limiting opening such that a sliding movement along side surfaces of the diaphragm leaves takes place by a number of diaphragm leaves which is reduced by at most one;
  b) setting a first aperture opening of the collimator suitable for irradiation of a first region of the tumor;
  c) irradiating the tumor;
  d) translating the collimator in a direction substantially transverse to said first radiation angle to scan the tumor;
  e) irradiating a further region of the tumor;
  f) repeating steps d) and e) until a desired region of the tumor is irradiated with the first aperture size;
  g) setting a further aperture opening of the collimator which differs from the first aperture opening;
  h) repeating steps d) through g) until a desired region of the tumor is irradiated;
  i) positioning the iris diaphragm collimator to irradiate the tumor from a second irradiation angle which differs from the first irradiation angle; and
  j) repeating steps b) through i) until a desired dose of radiation has been applied to the tumor.

The problem underlying the instant invention is also solved by a device for stereotactic, conformal radiation therapy of tumors, the device comprising: an iris diaphragm collimator having at least three diaphragm leaves, said diaphragm leaves defining a beam-limiting opening such that a sliding movement along side surfaces of said leaves takes place by a number of diaphragm leaves which is reduced by at most one; a mechanism for positioning said iris diaphragm to irradiate the tumor from an irradiation angle; a mechanism for setting an aperture opening of the collimator suitable for irradiation of a region of the tumor; a mechanism for irradiating the tumor; and a mechanism for translating the collimator in a direction substantially transverse to said radiation angle.

The basic concept of the invention is that an adjustable iris diaphragm can be brought more quickly to the required size than is possible by the changing of solid diaphragms. In contrast, relative to diaphragm leaves with several openings that can be brought into the beam path, it has both less weight and also greater flexibility with regard to the adjustable diaphragm opening width.

The construction is relatively simple and the positioning movement required for adjusting the diaphragm opening can be achieved with simple mechanical or electronic means. The compact construction also allows the collimator equipped with the iris diaphragm to be brought into the required positions by means of appropriate devices. This is required in the area of therapeutic radiation for scanning an area as well as for radiation directed onto the object to be treated from different solid angles.

The iris diaphragm is configured such that absolutely no overlapping of the diaphragm leaves is necessary. This is achieved by placing all of the diaphragm leaves in a plane and having their side surfaces touch each other. After a sliding movement of the diaphragm leaves to create the diaphragm opening, short front constitutive areas of the side surfaces of the diaphragm leaves are exposed, in order to limit the beam-limiting diaphragm opening formed in this way. Therefore, it is possible to also use iris diaphragms in the field of very high-energy beams, wherein a manageable overall height can be maintained despite the thickness of the diaphragm leaves required for the radiation shielding. Because no overlapping areas are required, the weight is less in comparison with a typical iris diaphragm construction. The weight, which is determined essentially by the shielding material, corresponds approximately to the weight of solid diaphragms.

Since scanning of a surface is to be performed by means of the collimator, a scanning device must be provided that scans an object to be treated by means of the beams limited by the iris diaphragm. The iris diaphragm is thereby selectively brought into the beam path at the required size. Another possibility of such a scanning device arises when the radiation source and iris diaphragm are located on a robot arm that can move around the object to be treated. Such robot arms are known. They are already used for numerous purposes, especially in automated production, so that their more detailed description can also be omitted.

During treatment, the opening can first be left large in order to scan an area and then made small and scanned with a scanning movement of arbitrary shape, such as, for example, the irregular edge regions of the surface of an object to be treated.

Radiation sources and collimators can, by means of a gantry, also be brought into various solid angle alignments of the beams limited by the collimator relative to the object to be treated. The scanning device is suspended in such a gantry in order to scan a spatial structure to be irradiated from different sides. Such gantries are already used in conventional radiation devices, especially in connection with multi-leaf collimators that simulate the area to be radiated by means of a complex mechanism.

The purpose of the invention is to provide a shielding capability for particularly high-energy radiation with a low overall height of an iris diaphragm. For such applications, the shielding capability for high-energy radiation should be designed in the megavolt range with regards to a radiation source. This then relates mainly to the field of application of radiation therapy, because, for example, such high-energy radiation is required to destroy tumor tissue. For this purpose, the thickness of the diaphragm leaves should lie between 6 and 10 cm, with typical diaphragm leaf material, such as a tungsten alloy, for example, being assumed.

In accordance with one aspect of the invention, one diaphragm leaf is fixed and the other diaphragm leaves slide by along the edge of an adjacent diaphragm leaf to form the opening. This embodiment has the advantage of simplifying the drive mechanism for the leaves while also permitting different aperture shapes to be generated which can be more closely matched to the shape and environment of the tumor.

For applications in which the center of the diaphragm opening is to always be at the same position irrespective of its size, it is useful for all of the diaphragm leaves to slide by an equal regulating distance so that, after the positioning movement, the opening is formed by partial areas of the side surfaces which have the same distance from the center. In this configuration, the optical axis always remains at the same position irrespective of the opening movement of the diaphragm leaves of the iris diaphragm.

What is necessary with regard to support of the diaphragm leaves depends on whether all of the diaphragm leaves perform a sliding movement and how many diaphragm leaves are provided. For only three diaphragm leaves, with one being fixed, a secure contact at the side surfaces of the stationary diaphragm leaf is sufficient for guiding the two sliding diaphragm leaves. In particular, if all of the diaphragm leaves can slide, a unique movement profile requires that the diaphragm leaves be supported by means of linear guides running in the direction of the sliding movement. With regard to the course of the linear guides, the exact course of the movement of each diaphragm leaf must be taken into account. This becomes clear in even more detail from the description of the figures. For example, it follows from a four-leaf diaphragm that the linear guides must run at a 45° angle with respect to the side surfaces contacting the other diaphragm leaves.

An especially useful configuration arises when the iris diaphragm has four diaphragm leaves. This produces a square opening which can be guided in a scanning movement across the area of an object to be treated, such that at the end of the scanning process, the radiation period is exactly equal to the total radiated area.

An iris diaphragm with four diaphragm leaves can also be equipped such that each side surface forming the opening transitions at its inner end maps into a tab-like, projecting, quarter-circle arc, which then forms the end of this side surface. If the four diaphragm leaves are joined such that the arcs touch directly, then a round opening is produced. Such a configuration is especially useful if a single beam with a very small diameter is needed for scanning or for point-by-point irradiation. If such diaphragm leaves are opened further, then a square opening with round corners is produced, wherein different sizes are possible. This can then be used for scanning using the method and means mentioned above. In this way, the greater part of an area can be scanned with the relatively large square openings, and then a very fine beam can be produced with the small round opening and used to scan irregular edge areas for which the square opening has too great a surface area.

Alternatively, the iris diaphragm can be designed such that a beam is formed that is as round as possible. For this purpose, at least six diaphragm leaves are preferred, wherein the approximation of a circular shape naturally improves more and more with a greater number of leaves. This enables a large opening to be formed, like that required, for example, for X-ray radiation for diagnostic purposes. Alternatively, a round tumor, such as, for example, a brain tumor, can be irradiated with high-energy radiation.

In the method and device according to the invention, it must be guaranteed that the side surfaces of the diaphragm leaves of the iris diaphragm touch each other exactly. Therefore, they must be exactly flat and may not exhibit any surface roughness. If necessary for this purpose, a microfinish is required such as, for example, grinding or lapping. It is further necessary that the side surfaces contact each other tightly, for which purpose it is proposed that force-applying devices be provided that press the side surfaces of the diaphragm leaves against each other. For example, springs functioning as the force-applying devices can act on the diaphragm leaves. An even better surface contact can be achieved through such force-applying devices than through precise guides, since guides must always exhibit a small amount of play.

Another possibility for good contact between the side surfaces arises when these have common guides, wherein the side surfaces of the diaphragm leaves adjacent to each other can be shifted relative to each other in their adjacent regions not used for forming the diaphragm opening. Such a common guide of two side surfaces of adjacent diaphragm leaves can also contain a force-applying device through springs for the purpose of a precise surface contact of the side surfaces.

The shifting movement of the diaphragm leaves is achieved in that at least one diaphragm leaf is driven. This is in particular sufficient for the already mentioned three-leaf iris diaphragm. If there are more diaphragm leaves, then, for example, every second diaphragm leaf can be driven and the other diaphragm leaves are entrained by this leaf by the force transmission produced thereby. However, for an opening movement that has the most friction-free and exact profile as possible, it is useful if all of the diaphragm leaves are driven simultaneously.

Such a simultaneous drive of all of the diaphragm leaves can be realized in various ways. For example, it is possible for a drive to be provided to each diaphragm leaf wherein simultaneous movement is realized by an electronic control. However, this must be very precise, because non-uniform driving would lead to the result that the diaphragm leaves become wedged in each other. In another possibility, one drive simultaneously drives all of the diaphragm leaves by means of a mechanism. Such mechanisms can be formed in various ways. For example, spindle or worm drives can be provided, which are moved simultaneously by means of a transmission. Another possibility consists in that the mechanism has a cam disk that can rotate about the center of the diaphragm opening, wherein an opening in the center of the cam disk is naturally required that permits passage of the greatest possible portion of the beam. Spiral-shaped adjusting cams that activate the diaphragm leaves are then arranged on this cam disk. The adjusting cams can be grooves or raised sections that adjust the diaphragm leaves by means of elements which are arranged on these diaphragm leaves and slide on the adjusting cams.

In another possibility for the construction of such a mechanism, there is a regulating element that can rotate about the center of the diaphragm opening and that acts on each diaphragm leaf with a regulating arm. Naturally, it is then useful if such a sliding motion also includes a return by means of the regulating arms. This can be realized, for example, through restoring springs acting in the direction opposite to the positioning movement.

As already mentioned, the side surfaces of the diaphragms must contact each other absolutely plane-parallel, because otherwise a gap is produced through which stray radiation can pass. This must be prevented since such stray radiation would fall upon healthy tissue. Because a very small gap cannot be completely avoided even by means of the most precise surface treatment over the entire area of the adjacent surfaces, it is useful if the adjacent side surfaces extend such that the gap is not parallel to the beam path. In this way, in the sliding direction, the side surfaces can have deviations from the flatness of the side surfaces that engage in complementary fashion. It is known to provide steps or the like for this purpose. Therefore, these configurations are not discussed in more detail. A good solution for preventing the mentioned stray radiation arises for the iris diaphragm according to the invention when this is tilted relative to an imaginary collimator plane lying perpendicular to the optical axis of the radiation, such that a beam can no longer pass through a possible gap. Since high precision tolerances of the surfaces lead to possible gaps in the micrometer range, a corresponding small tilt of arc seconds is sufficient. This has practically no effect on the beam formation.

Naturally, in addition to the field of very high-energy radiation, the collimator according to the invention can also be used for X-ray devices, the advantages of non-overlapping diaphragm leaves also being relevant in these devices, since a small overall height is advantageous for any device.

In order to achieve additional shielding, in addition to the iris diaphragm, the collimator according to the invention also has a fixed diaphragm, which is located in the beam path and whose opening is adjusted to the greatest possible opening of the iris diaphragm.

The invention will be explained below with reference to the embodiments shown in the drawing.

BRIEF DESCRIPTION OF THE DRAWING

FIG. 1a shows a simple embodiment of a three-leaf iris diaphragm 5 for explaining the principle. A three-leaf iris diaphragm 5 was selected for this explanation because it can be most clearly illustrated due to the small number of parts. This iris diaphragm 5 is provided with three diaphragm leaves 6, 6', and 6". For this embodiment, the diaphragm leaf 6 is fixed and the diaphragm leaves 6' and 6" can move in the direction of the arrow 13. In the closed state of the iris diaphragm 5, the angles α are located at the center 11, wherein each angle α is formed by two side surfaces 10 of the diaphragm sheets 6, 6', 6". These angles α naturally become correspondingly smaller for iris diaphragms 5 with more diaphragm leaves.

Figure 1A:
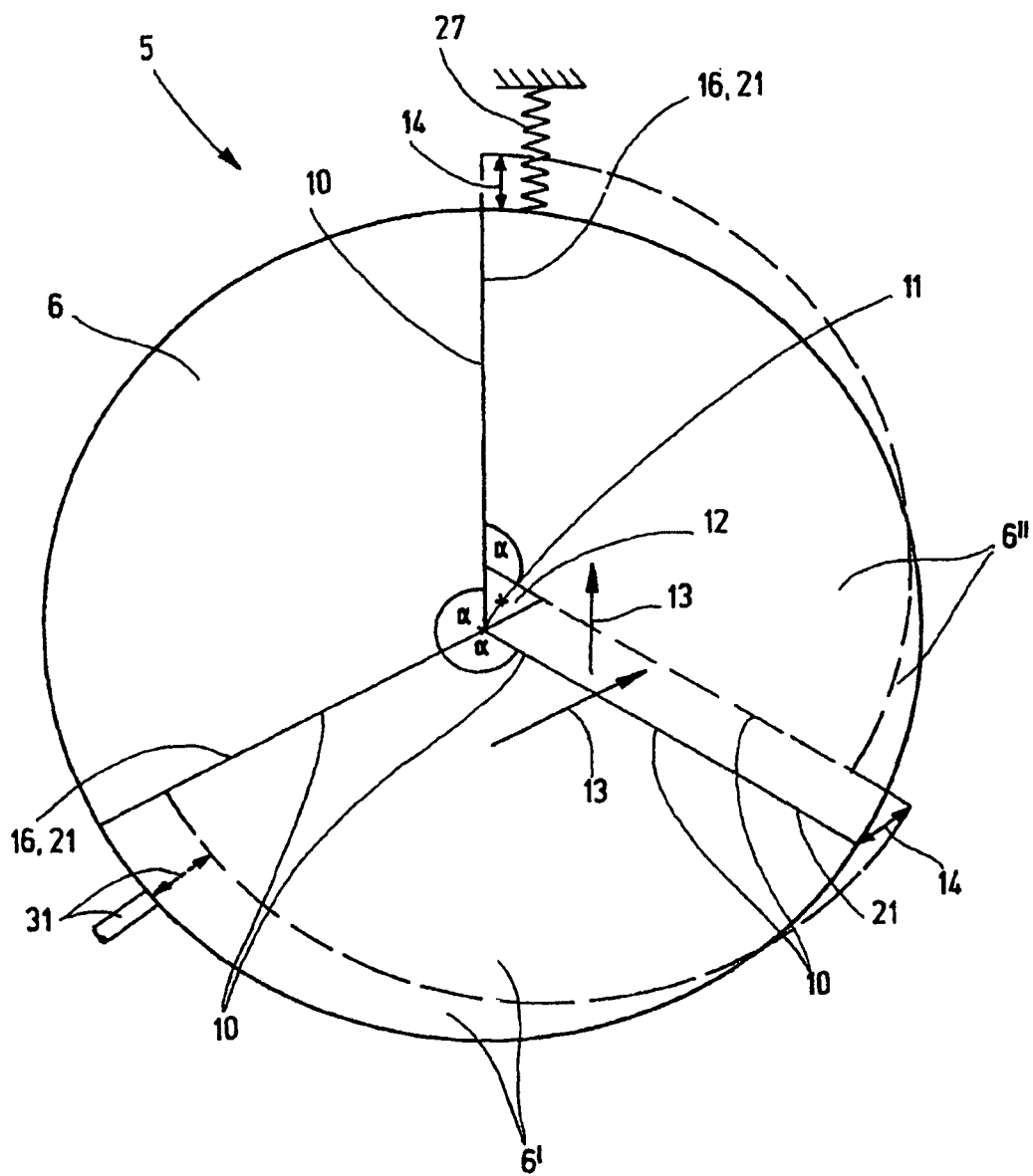
FIG. 1a a simple embodiment of a three-leaf iris diaphragm for explaining the principle.

In this embodiment, the diaphragm leaves 6' and 6" are guided by means of guides 21 on the side surfaces 10, such that the side surfaces 10 contact each other tightly. In this way, due to the fixed arrangement of the diaphragm leaf 6, its side edges 10 form linear guides 16 for the two other diaphragm leaves 6' and 6" and the guide 21 between these two leaves is shifted with these diaphragm leaves 6' and 6", wherein these complete the adjustment paths 14. A drive 31 shown symbolically on the diaphragm leaf 6' is used for this shifting, and a restoring spring 27 on the diaphragm leaf 6" is used for the return movement. A diaphragm opening 12 is opened by means of the shifting movement 13, with the size of the diaphragm opening 12 being governed according to the extent of the adjustment paths 14 traveled.

More favorable than a triangular diaphragm opening 12 is a square or a nearly round shape. These are exhibited by embodiments illustrated and described below. Furthermore, a configuration in which the center 11 does not shift with the opening of the iris diaphragm 5, as indicated here with the two small crosses, but rather this center point 11 remains steady when the iris diaphragm 5 opens, is possible. For this purpose, however, all of the diaphragm leaves must perform a shifting movement 13, and it is therefore necessary that these diaphragm leaves be supported by means of corresponding linear guides. This will also be explained in the embodiments below.

Figure 1B:
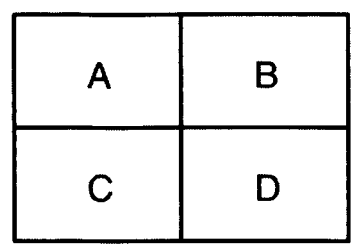
FIG. 1b a four leaf iris diaphragm in a first position.
Figure 1C:
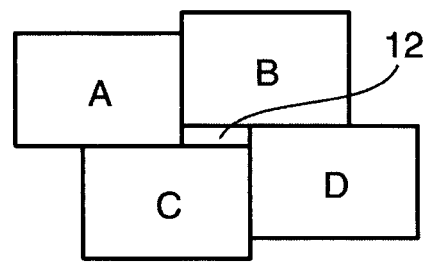
FIG. 1c the four leaf iris diaphragm of FIG. 1b in a second position.
Figure 1D:
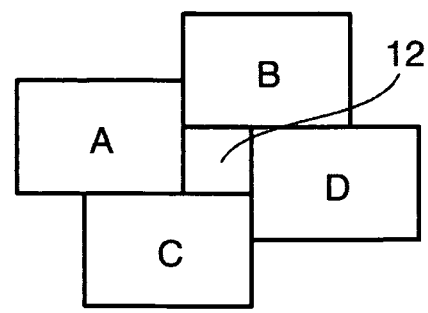
FIG. 1d the four leaf iris diaphragm of FIG. 1a in a third position.

FIGS. 1b to 1d show an embodiment in accordance with the invention for a four leaf collimator corresponding to the embodiment of FIG. 1a. Towards this end, the leaf A is fixed and leaves B through D are moveable. FIG. 1b shows the collimator in a closed position. FIG. 1c shows a configuration of the collimator in which the leaves define a rectangular, horizontal aperture 12. In FIG. 1d, leaves B through D are displaced to define a substantially square aperture 12. Since leaf A is fixed, leaf C need only be displaced in the horizontal direction and leaf B merely in the vertical direction. Only leaf D must be displaced both horizontally and vertically. However, since leaf D is sandwiched between leaves B and C, it is automatically driven when those leaves are moved. Consequently, only a suitable mechanism is needed to load leaf D against the edges of leaves C and B (i.e. a spring). The drive mechanism for the collimator is therefore highly simplified. Inspection of FIGS. 1b to 1d also shows that apertures of variable width and arbitrary rectangular shape can be generated. This principle can be extended to an arbitrary number of leaves in which only one leaf is fixed.

Figure 2:
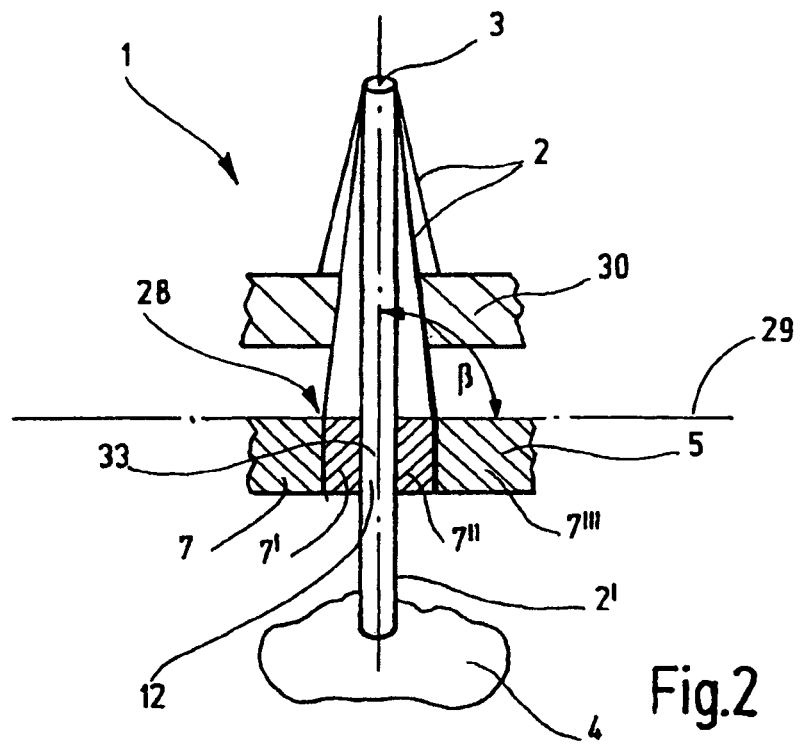
FIG. 2 a schematic diagram of the collimator.

FIG. 2 shows a schematic diagram of the collimator 1 with an iris diaphragm 5. The collimator 1 is associated with a radiation source 3 from which radiation 2 emerges. Arranged before the iris diaphragm 5 is a fixed diaphragm 30, which has an opening corresponding to the largest possible opening of the iris diaphragm 5. This fixed diaphragm 30 is used to limit the radiation 2 of the radiation source 3 and to prevent as much as possible the occurrence of stray radiation. Here, the iris diaphragm 5 is shown in a sectional view, wherein it concerns a four-leaf iris diaphragm 5 with diaphragm leaves 7, 7', 7", 7'". This is shown in greater detail below. The radiation 2 is further narrowed to the radiation 2' by means of the opening 12 of the iris diaphragm 5 such that the surface of an object 4 to be treated can be scanned, for example, with this radiation 2', DE 101 57 523 C1 being referenced with regard to such a scanning device. Such a scanning device can in turn be arranged on a gantry, so that it is possible to irradiate the object 4 to be treated from various sides and to thereby achieve maximum irradiation, for example, of a tumor, with the surrounding tissue simultaneously receiving significantly less radiation.

Figure 3:
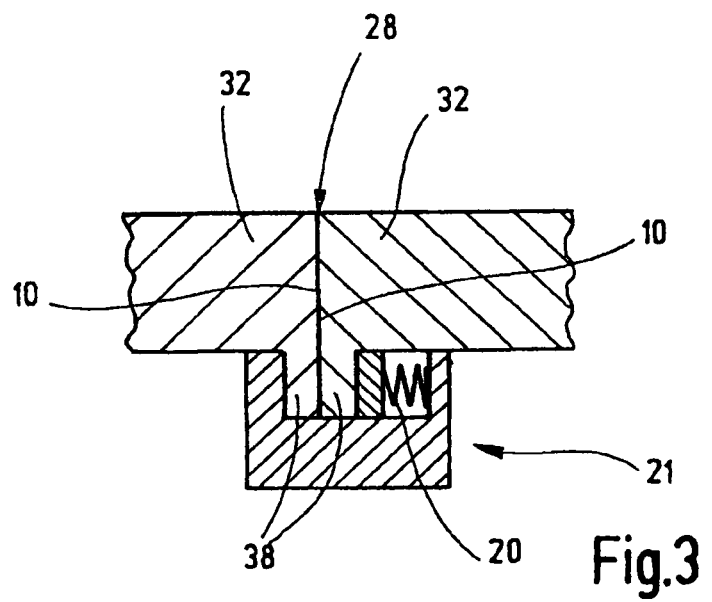
FIG. 3 a guide on the side surfaces of the diaphragm leaves.

FIG. 3 shows a detail of a guide 21 between two diaphragm leaves 32. The diaphragm leaves 32 can be arbitrary diaphragm leaves, embodied as in this description, or naturally also an iris diaphragm 5 that has even more diaphragm leaves. The guide 21 shown here is used to hold two diaphragm leaves 32 tightly together with their side surfaces 10, such that no or nearly no gap 28 is produced. Springs 20, which are arranged in the guide 21 and which press together projections 38 joined to the diaphragm leaves 32, are also used for this purpose. Such guides 21 can naturally be arranged only in the regions of the side surfaces 10 which are not used as partial regions 15 for forming a diaphragm opening 12.

Because a gap 28 can never be completely prevented, it is proposed that the diaphragm plane 29 indicated in FIG. 2 be slightly tilted relative to the optical axis 33, such that no radiation 2 can pass through a gap 28 between diaphragm leaves 32. That is, the angle β has a slight deviation from 90°, with a few arc seconds being sufficient, as a rule. In addition, it is to be noted that the beam path is shown significantly shortened in FIG. 2. Actually, the distance to the radiation source 3 in relation to the diaphragm opening 12 is significantly larger, the radiation 2 in the region of the iris diaphragm 5 having only a minimal deviation from a parallel course so that, in contrast to the illustration of FIG. 2, a passage of radiation 2 through a gap 28 is possible and therefore should be stopped by the described tilting or other means. The tilting can be very minimal, however, since the high surface quality and flatness of the side surfaces 10 allow only a gap 28 in the micrometer range to occur in any case.

Figure 4A:
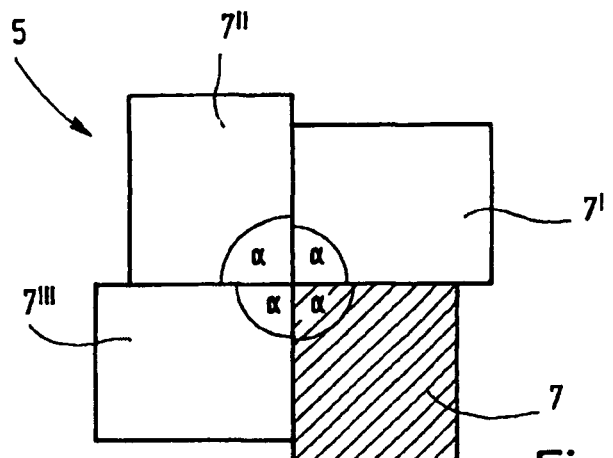
FIGS. 4a, 4b, and 4c a schematic diagram of a four-leaf iris diaphragm.
Figure 4B:
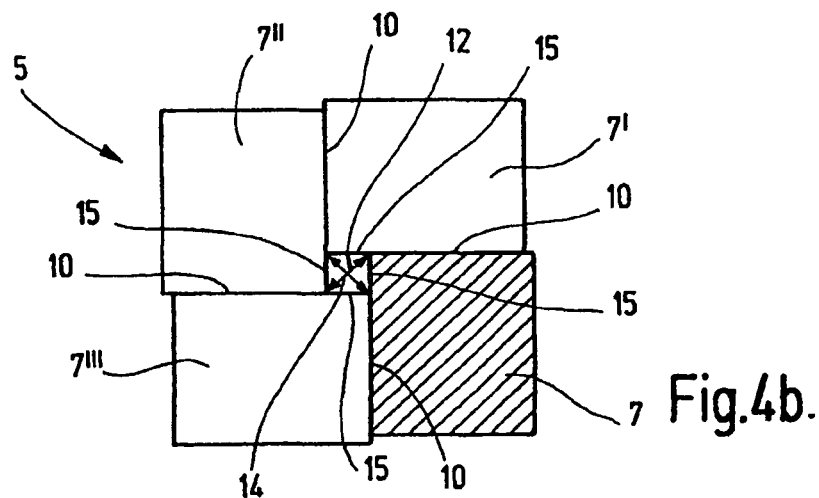
Figure 4C:
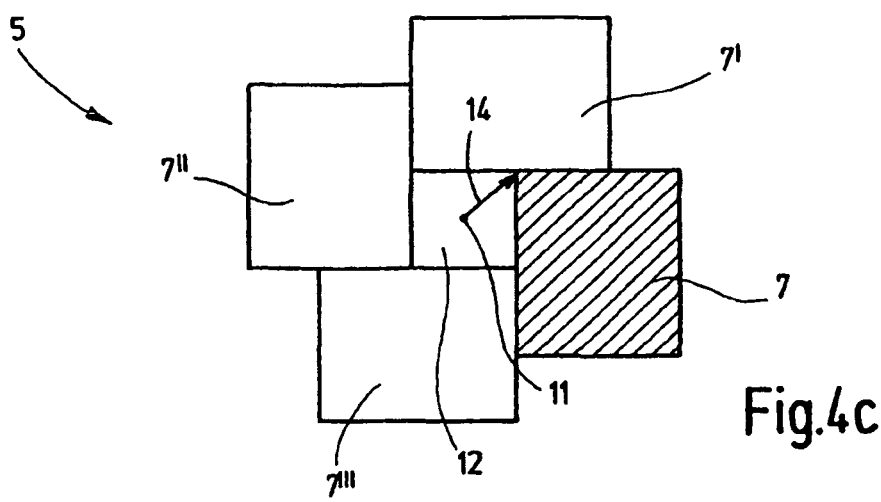

FIGS. 4a, 4b, and 4c show a schematic diagram of a four-leaf iris diaphragm 5 having the diaphragm leaves 7, 7', 7", and 7'". In FIG. 4a, the iris diaphragm 5 is closed, wherein the angles α, which are right angles, contact each other. In FIG. 4b, all of the diaphragm leaves have moved by the same adjustment path 14, so that an opening 12 is produced which is formed by partial regions 15 of the side surfaces 10 of the diaphragm leaves 7, 7', 7", 7'". The adjustment paths 14 each correspond to half the two diagonals of the square opening 12.

FIG. 4c shows another opening of the iris diaphragm 5, wherein the center 11, which lies in the optical axis 33 (see FIG. 2), is marked, and the adjustment path 14 completed by the top left corner of the diaphragm leaf 7 projects from this point. In a corresponding way, the other diaphragm leaves 7', 7", 7'" have also completed adjustment paths 14.

Figure 5A:
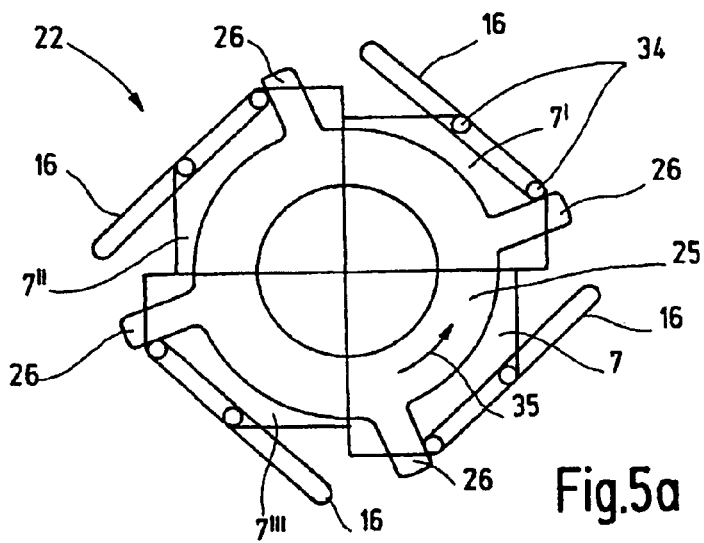
FIGS. 5a, 5b, and 5c an embodiment of a mechanism for simultaneous adjustment of the diaphragm leaves.
Figure 5B:
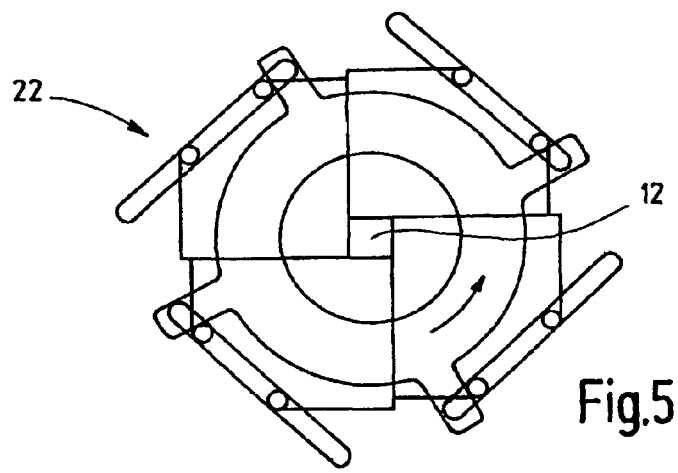
Figure 5C:
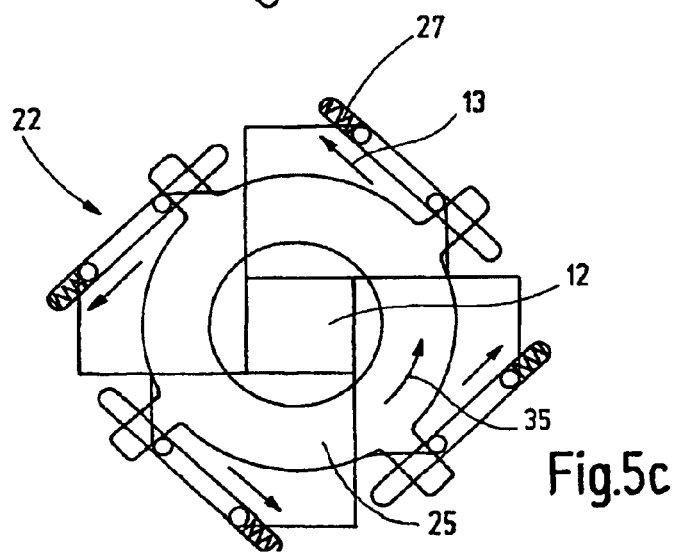

FIGS. 5a, 5b, and 5c show an embodiment of a mechanism 22 for simultaneous adjustment of diaphragm leaves. This embodiment is illustrated with reference to four diaphragm leaves 7, 7', 7", and 7'". The mechanism 22 has a regulating element 25, which provides regulating arms 26 which are each assigned to one of the diaphragm leaves 7, 7', 7", and 7'". The diaphragm leaves 7, 7', 7", and 7'" have guide pins 34, with each leaf having two pins that are supported in linear guides 16. When the regulating element 25 rotates in the direction of the arrow 35, the regulating arms 26 shift the pins 34 along the linear guides 16, thus realizing the adjustment paths 14 of the diaphragm leaves 7, 7', 7'', 7''' described above.

FIG. 5*b* already shows an opening 12, which is opened even further in FIG. 5*c*. In FIG. 5*c*, the shifting movements 13 are also marked, as well as the possible arrangement of restoring springs 27 that can close the iris diaphragm 5 again when the regulating element 25 is moved back opposite to the direction of the arrow 35.

Figure 6A:
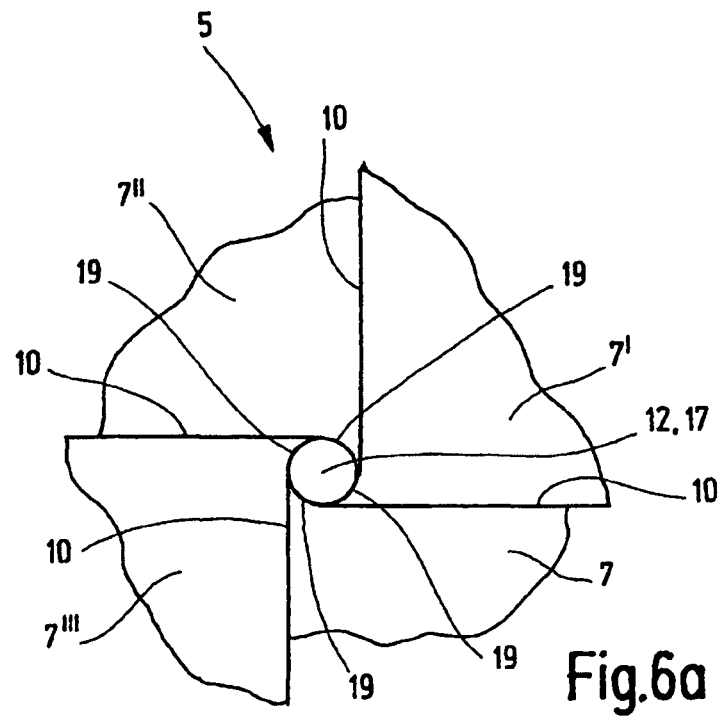
FIGS. 6a and 6b another embodiment of a four-leaf iris diaphragm.
Figure 6B:
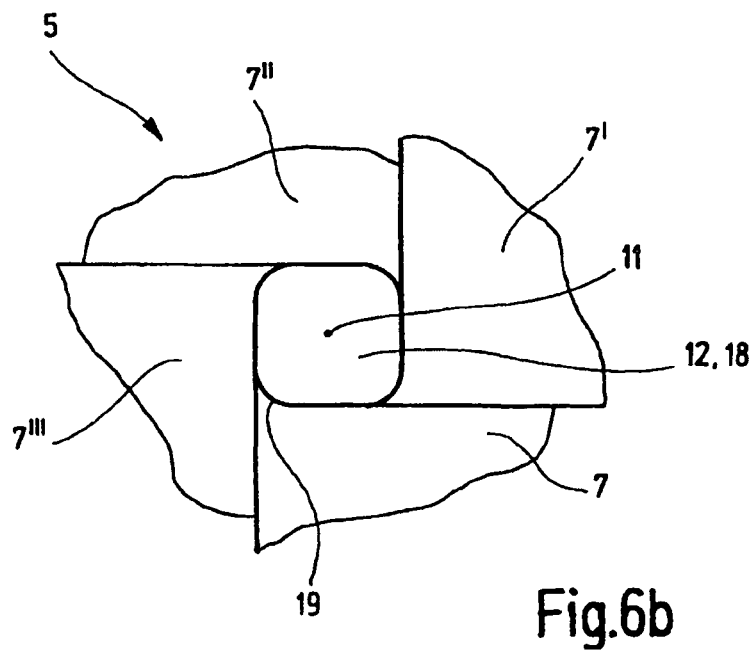

FIGS. 6*a* and 6*b* show another possible configuration of a four-leaf iris diaphragm 5. Here the diaphragm leaves 7, 7', 7'', and 7''' have tab-like, projecting circular arcs 19 at the front ends of their side surfaces 10. In this possible configuration, the iris diaphragm 5 cannot be closed completely because a positioning movement 13 is possible here only up to the point that the circular arcs 19, which are each a quarter circle, join together to form a round opening 17. This is then the smallest possible opening 12. If this iris diaphragm 5 is opened in a way corresponding to that described above, then a square opening 18 is produced in which the circular arcs 19 form rounded corners. This is shown in FIG. 6*b*. The advantages of such a configuration have already been mentioned above.

Figure 7A:
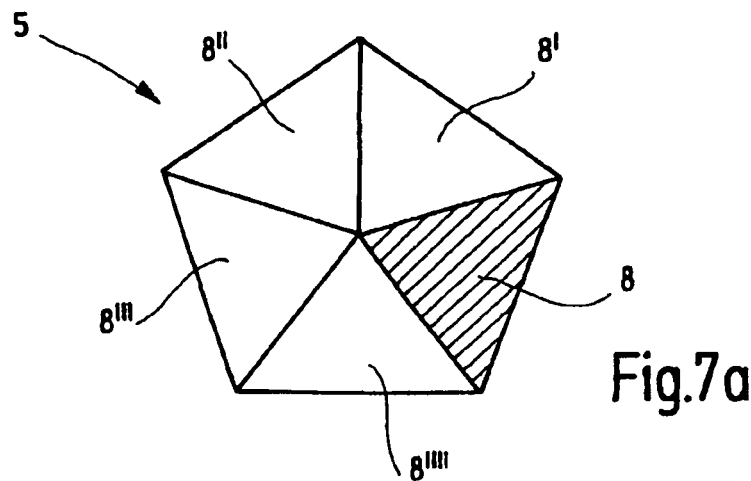
FIGS. 7a, 7b, and 7c a schematic diagram of a five-leaf iris diaphragm.
Figure 7B:
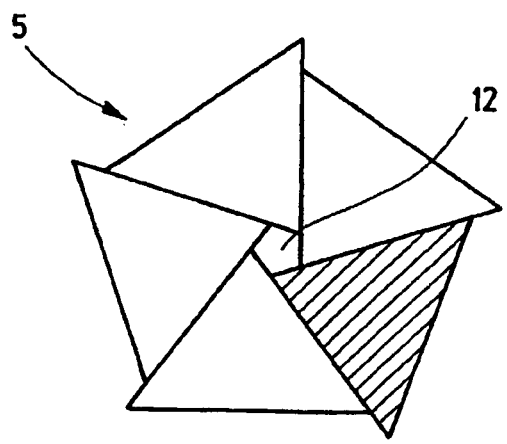
Figure 7C:
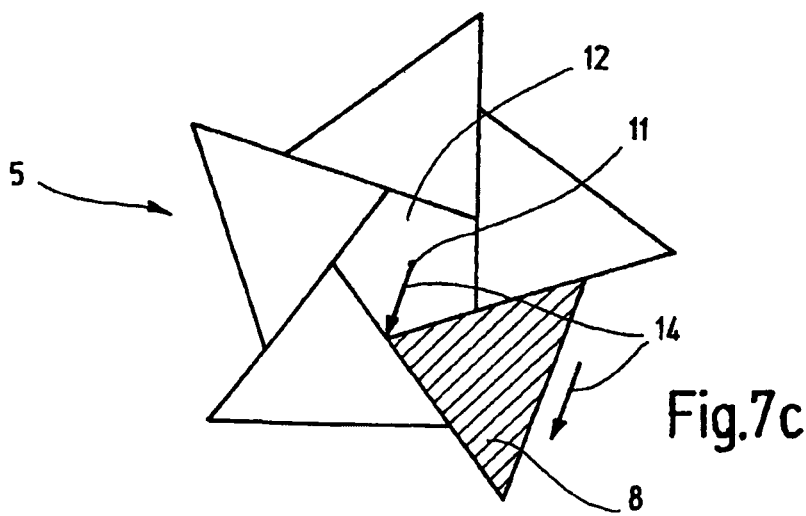

FIGS. 7*a*, 7*b*, and 7*c* show a schematic diagram of a five-leaf iris diaphragm 5. Here, all of the diaphragm leaves 8, 8', 8'', 8''', and 8'''' complete simultaneous positioning movements in order to form an opening 12, as shown in FIGS. 7*b* and 7*c*. FIG. 7*c* makes more clear the adjustment path 14 that is completed, for example, by the diaphragm leaf 8 highlighted with shading, wherein the adjustment path 14 starting from the center 11 describes the path completed by the corner of the diaphragm leaf 8 that now lies at the tip of the arrow.

Figure 8A:
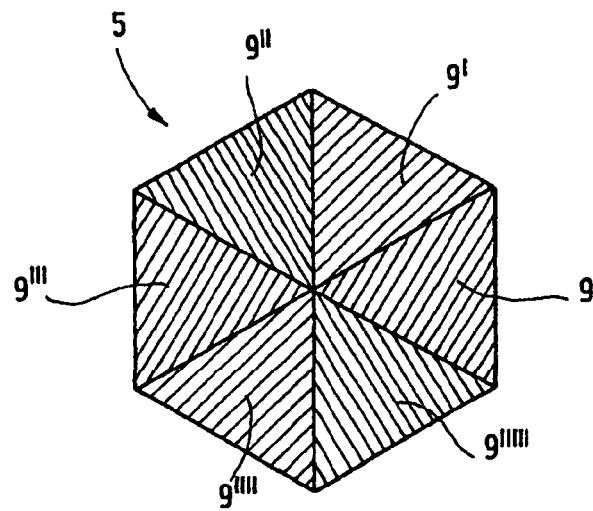
FIGS. 8a, 8b, and 8c a schematic diagram of a six-leaf iris diaphragm.
Figure 8B:
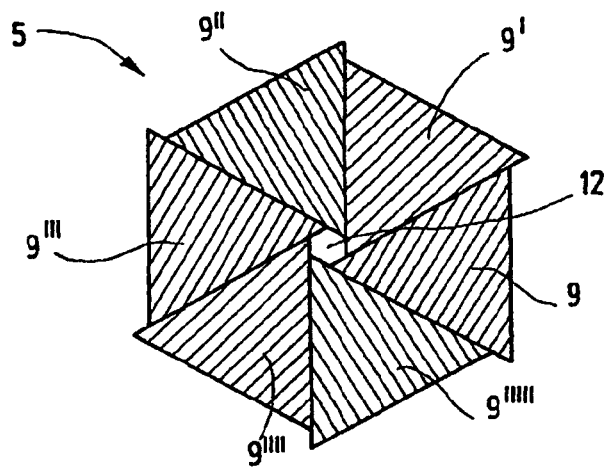
Figure 8C:
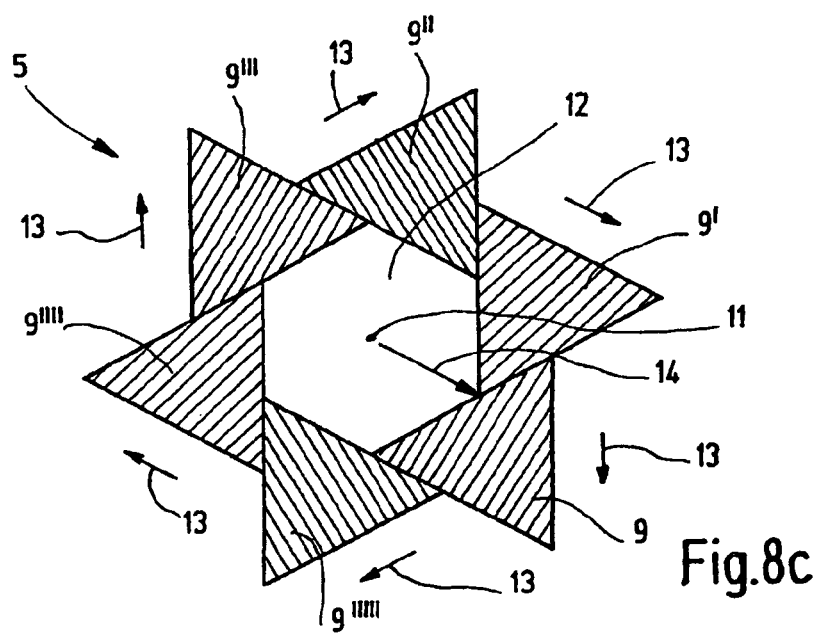

FIGS. 8*a*, 8*b*, and 8*c* show a schematic diagram of a six-leaf iris diaphragm 5. The representations correspond to the previously explained representations, wherein the diaphragm leaves 9, 9', 9'', 9''', 9'''', and 9''''' are drawn with various shadings so that the positions of these diaphragm leaves can be more easily identified in the opening movements shown with FIGS. 8*b* and 8*c*. In FIG. 8*c*, the shifting movement of each of the diaphragm leaves 9, 9', 9'', 9''', 9'''', and 9''''' is marked with the arrows 13. The adjustment path 14 is illustrated with an arrow starting from the center 11 for the corner at the tip of the arrow, which belongs to the diaphragm leaf 9'.

Figure 9:
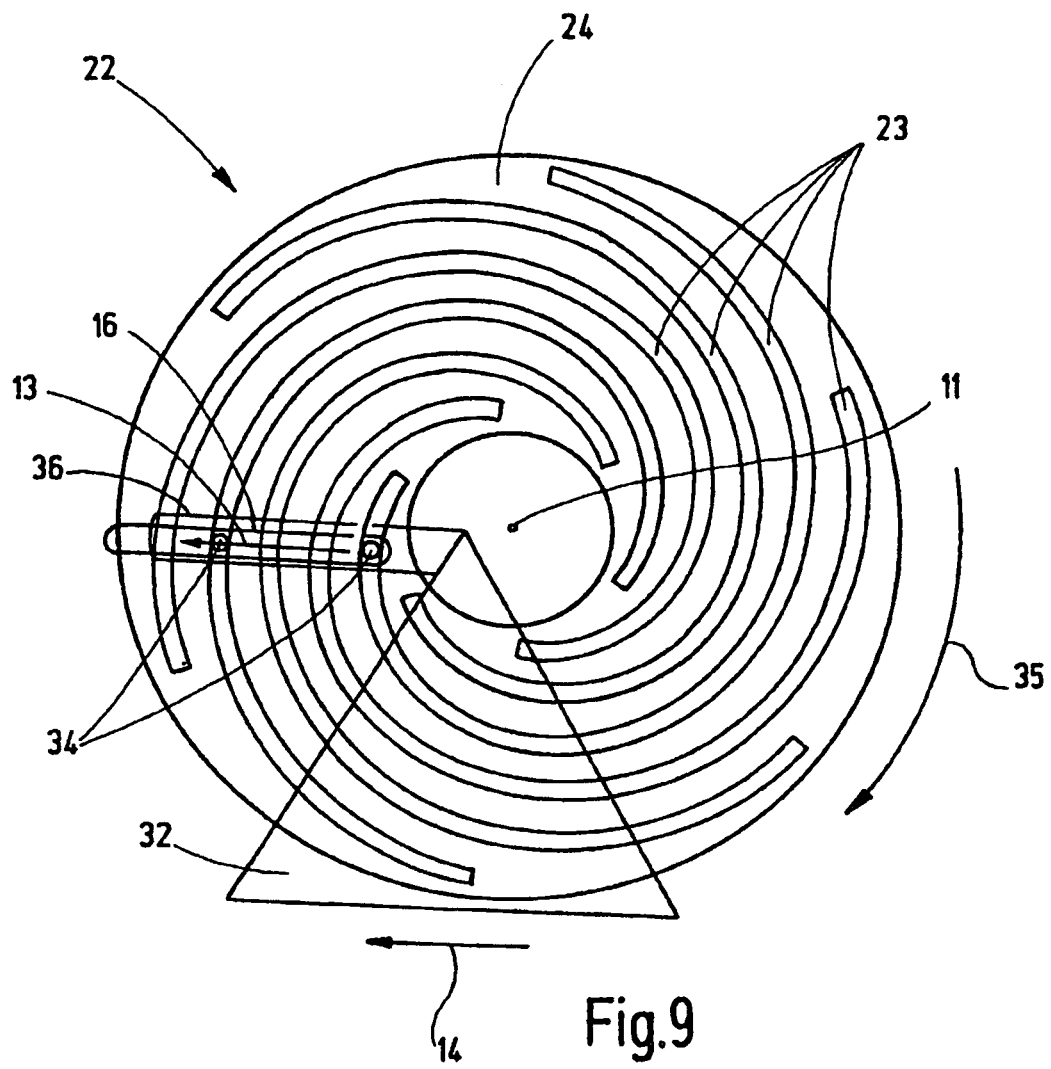
FIG. 9 another embodiment of a mechanism for simultaneous adjustment of diaphragm leaves.
Figure 9A:
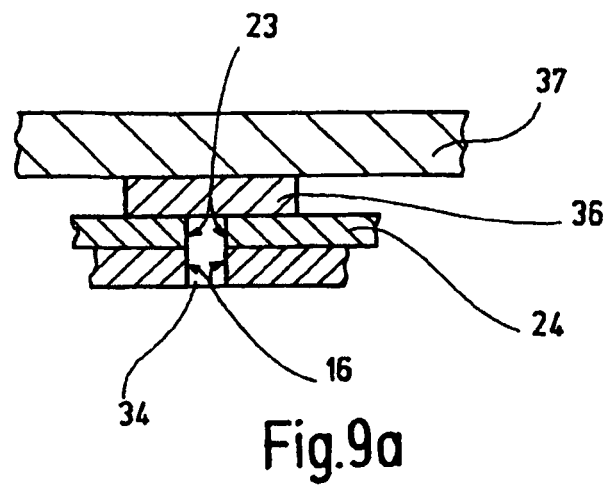
FIG. 9a a detail of this mechanism.

FIG. 9 shows another embodiment of a mechanism 22 for simultaneous adjustment of diaphragm leaves, wherein FIG. 9*a* shows a detail of this mechanism 22 as a section perpendicular to a retaining arm 36. In the embodiment, a cam disk 24 is involved, which has adjusting cams 23. The diaphragm leaves 32—which can be embodied arbitrarily—are here each equipped with a retaining arm 36, each of which carries two guide pins 34. Here, the representation is limited to one diaphragm leaf 32. The guide pins 34 extend through the adjusting cams 23 of the cam disk 24 embodied as grooves, and also run in linear guides 16. In this way, rotation of the cam disk 24 in the direction of the arrow 35 causes the diaphragm leaf 32 to complete a shifting movement in the direction of the arrow 13. In contrast, if the cam disk 24 moves opposite the arrow 35, then the diaphragm leaf 32 moves back again opposite the adjustment path 14. All of the arranged diaphragm leaves 32 then always complete these adjustment paths 14 simultaneously.

It was not stated here how many diaphragm leaves are present, because such cam disks 24 can be used for a nearly arbitrary number of diaphragm leaves 32. The number and the course of the adjusting cams 23 depend on the number of diaphragm leaves 32 and the desired opening 12, and thus on the desired adjustment paths 14. Here, FIG. 9*a* also shows a cover plate 37, which advantageously covers the mechanism 22. Instead of the retaining arm 36, a corresponding arrangement of the guide pins 34 directly on each diaphragm leaf 32 can naturally also be performed.

The illustrated embodiments merely represent a small sample of possibilities. In particular, the support and adjustment mechanism can also be formed in other ways, as has already been mentioned above. In particular, it is also possible to increase the number of diaphragm leaves further in order to achieve a configuration of the diaphragm opening 12 that is as round as possible. Also, e.g., instead of the guides 21 on the side surfaces 10, dove-tailed guides could also be provided, if these are only arranged in the regions, which are not used for forming the opening 12. The springs 20 could also be arranged on the outer sides of the diaphragm leaves 6, 6', 6'', or 7, 7', 7'', 7''', or 8, 8', 8'', 8''', 8'''', or 9, 9', 9'', 9''', 9'''', 9''''' in order to press each against the side surfaces 10 of the two adjacent diaphragm leaves. Another possibility for achieving a good mutual holding of the side surfaces 10 would be an elastic enclosure of all diaphragm leaves of an iris diaphragm 5. Numerous other configuration possibilities are also conceivable.

Figure 10:
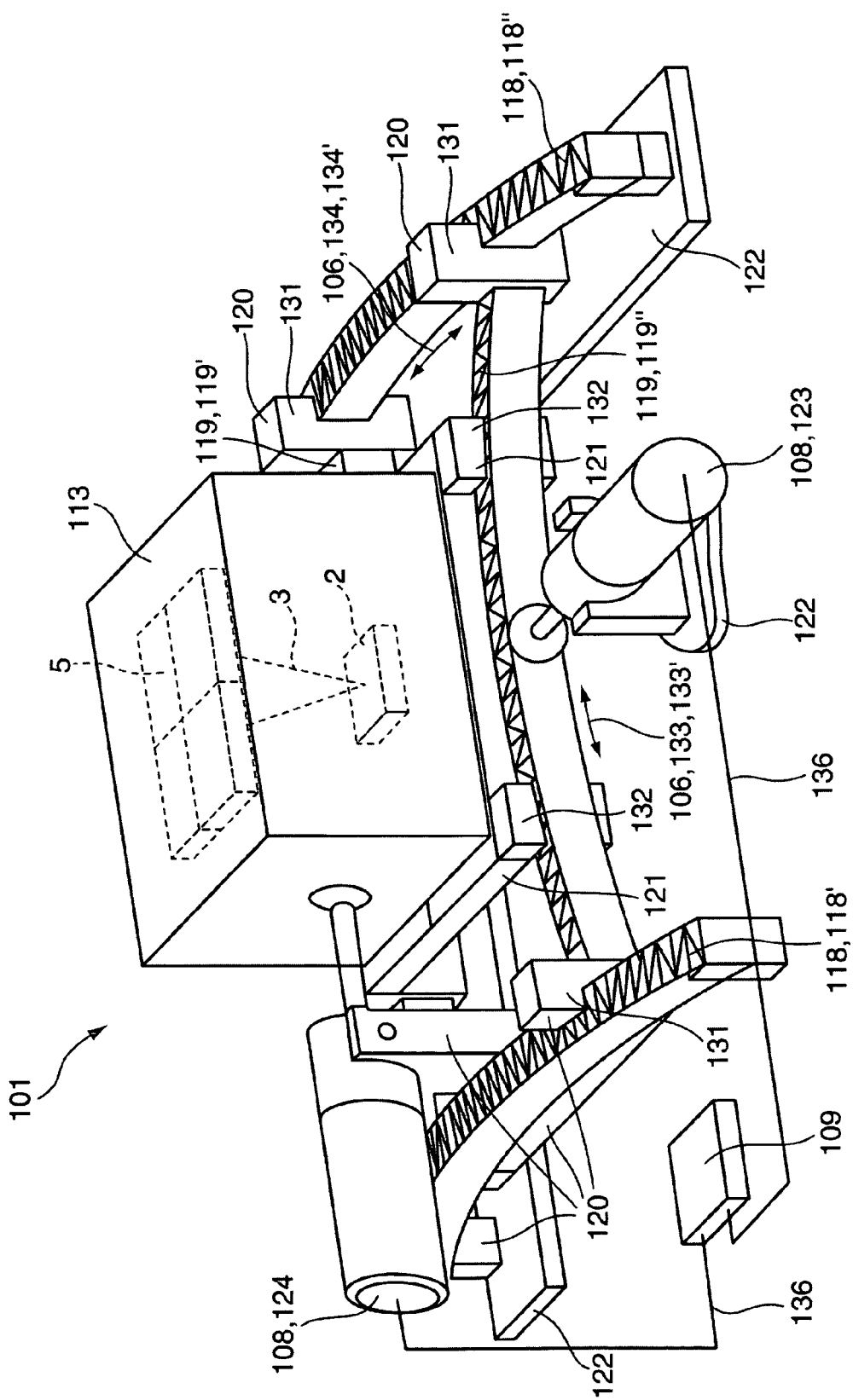
FIG. 10 a perspective view of a scanning device in accordance with the invention.

FIG. 10 shows an embodiment of a scanning device 101 in accordance with the invention in perspective view. The radiation source 3 is located below the collimator 5 and the beams 2 impinge on the collimator 5 from this direction. This embodiment shows realization of a drive 108. To permit motion along a path 106, a first sliding rail 118 is initially disposed in a collimator housing 122 (only partially shown). This first sliding rail 118 consists of a rail pair 118' and 118''. A first displaceable carriage 120 is disposed on this first sliding rail 118 which has bearings 131 which run on the first sliding rail 118. A second rail pair 119' and 119'' form a second sliding rail 119 which extends substantially perpendicular to the first sliding rail 118. A second carriage 121 is disposed on the second sliding rail 119 and can be displaced via bearings 132. The housing 113 carries the collimator 5 and source 3 and is located on this second carriage 121.

The two carriages 120 and 121 permit displacement along the path 106. Scanning motions 133, 133' in an x-direction and 134, 134' in a y-direction are thereby possible. A drive 123 for the first carriage 120 is disposed on the collimator housing 122. This drive performs the scanning motions 134, 134'. A drive 124 for the second carriage 121 is disposed on the first carriage 120 and provides displacement in the x-direction, i.e. executes scanning motions 133 and 133'.

To provide scanning motions 133, 133', 134, 134' such that a radiation surface can be exposed to the predetermined radiation, a control unit 109 is provided which is connected to the drives 123 and 124 via the connections 136.

Figure 11:
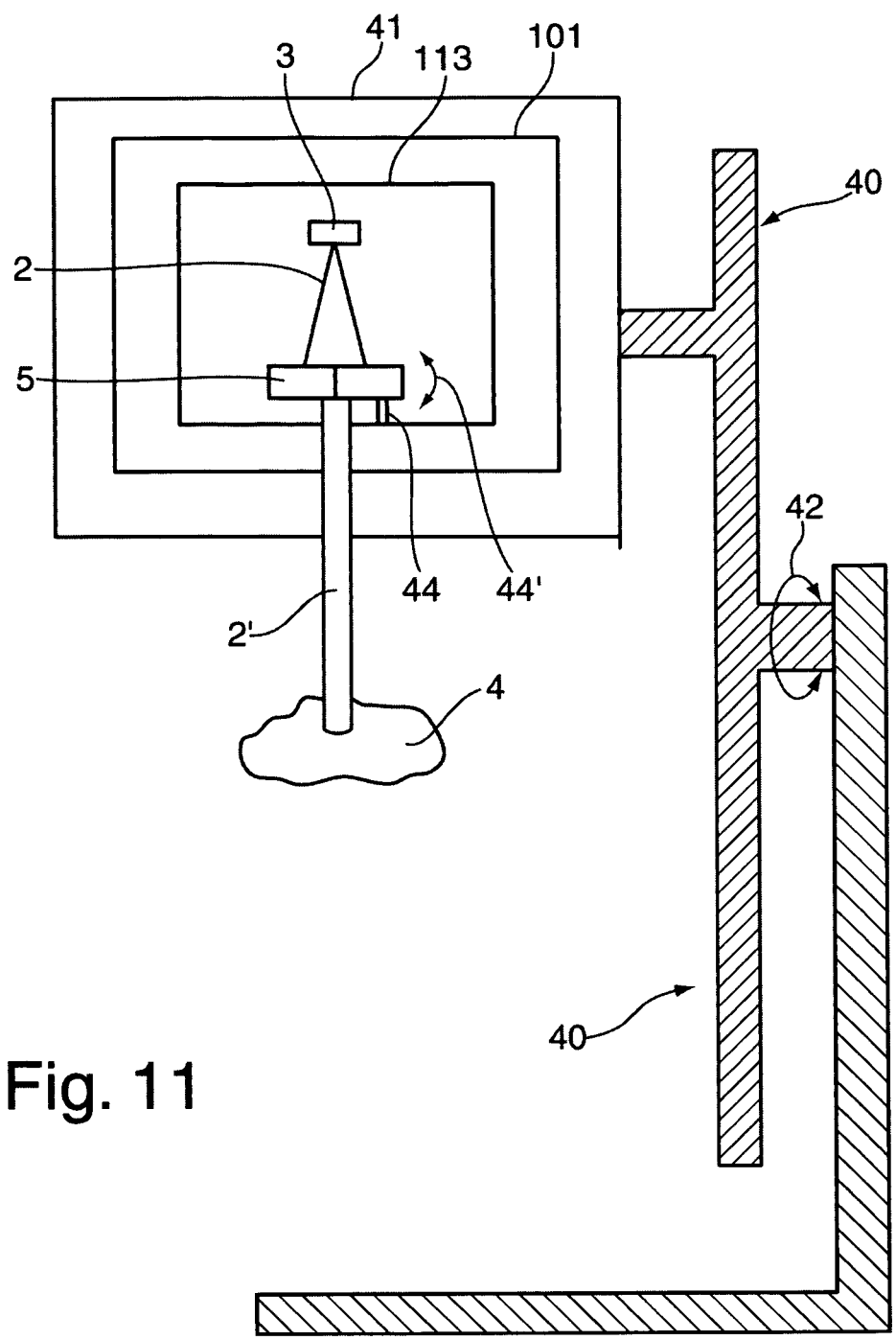
FIG. 11 a schematic view of a gantry for use in the method and device in accordance with the invention.

FIG. 11 indicates a preferred embodiment of the invention having a gantry 40 on which housing 41 is mounted, with scanning device 101, radiation source 3 and the iris diaphragm 5. The gantry 40 provides for motion of the source 3 and the iris diaphragm 5 about the object 4 being irradiated, as schematically indicated by arrow 42. In this manner, the radiation source 3 and iris diaphragm 5 can be brought into various solid angle alignments of the radiation beam 2 relative to the object being treated. The iris diaphragm 5 can also be tilted (schematically indicated by reference symbols 44 and 44') such that the radiation beam 2 can no longer pass through gaps between adjacent blades of the iris diaphragm.

Figure 12:
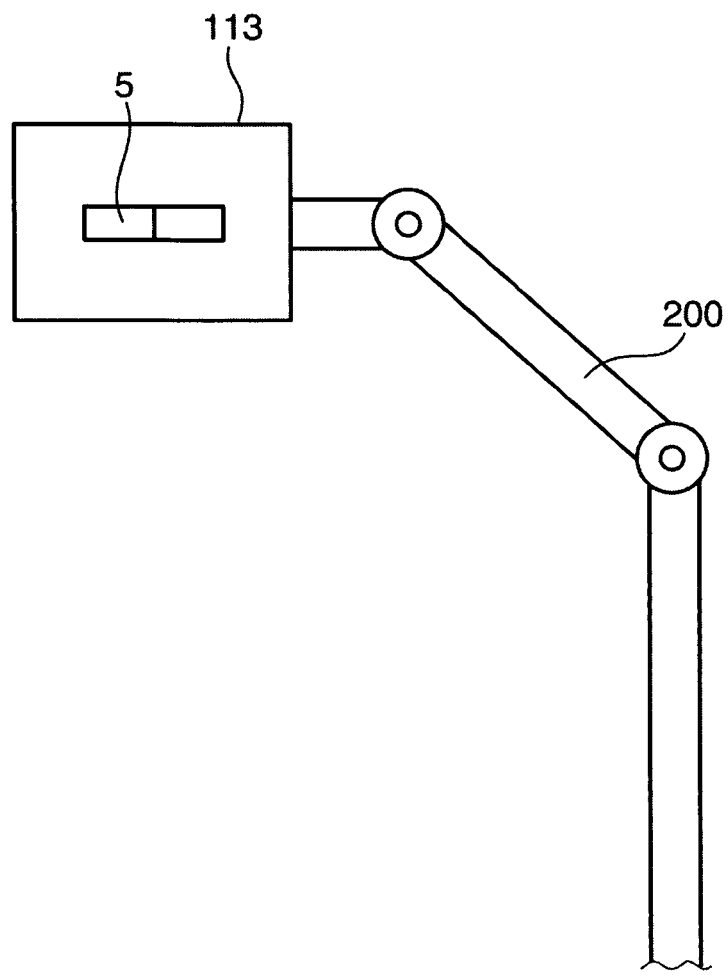
FIG. 12 a schematic view of a robot arm in accordance with the invention.

FIG. 12 shows an embodiment of the invention in which a robot arm 200 directly supports the housing 113 bearing the collimator 5 and source 3. In this embodiment, the robot arm 200 assumes the functions of the gantry 40 illustrated in FIG. 11 and the scanning mechanism 101 illustrated in FIG. 10.

LIST OF REFERENCE SYMBOLS

1 Collimator
2 Radiation
2' Radiation limited by the collimator
3 Radiation source
4 Object to be treated (diagnosis or radiation therapy)
5 Iris diaphragm
6, 6', 6" Diaphragm leaves in a three-leaf iris diaphragm
7, 7', 7", 7'" Diaphragm leaves in a four-leaf iris diaphragm
8, 8', 8", 8'", 8"" Diaphragm leaves in a five-leaf iris diaphragm
9, 9', 9", 9'", 9"" Diaphragm leaves in a six-leaf iris diaphragm
10 Side surfaces
11 Center
12 Opening/diaphragm opening
13 Arrows: shifting movement
14 Adjustment paths
15 Sub-areas of the side surfaces, which form the opening
16 Linear guides
17 Round opening
18 Square opening with rounded corners
19 Circular arc (tab-like, projecting)
20 Springs
21 Guides on the side surfaces
22 Mechanism
23 Adjusting cams
24 Cam disk
25 Regulating element
26 Regulating arms
27 Restoring springs
28 Gap (dependent on tolerances)
29 Diaphragm plane
30 Fixed diaphragm
31 Drive (symbolic)
32 Arbitrary diaphragm leaves
33 Optical axis
34 Guide pins on the diaphragm leaves
35 Arrow: direction of rotation of cam disk or adjusting element
36 Retaining arm of a diaphragm leaf
37 Cover plate
38 Projections
40 gantry
41 housing
42 arrow
44 tilt mechanism
101 scanning device
106 path
108 drive
109 control unit
113 housing
118, 118', 118" first sliding rail
119, 119', 119" second sliding rail
120 first displaceable carriage
121 second carriage
122 collimator housing
124 drive
131 bearings
132 bearings
133, 133' scanning motions
134, 134' scanning motions
136 connections
200 robot arm
α Angle between the side surfaces of the diaphragm leaves
β Angle between the optical axis and diaphragm plane

I claim:

1. A method for stereotactic, conformal radiation therapy of tumors, the method comprising the steps of:
   a) positioning an iris diaphragm collimator to irradiate the tumor from a first irradiation angle, the iris diaphragm having at least three diaphragm leaves, wherein the diaphragm leaves open up a beam-limiting opening such that a sliding movement along side surfaces of the diaphragm leaves takes place by a number of diaphragm leaves which is reduced by at most one;
   b) setting a first aperture opening of the collimator suitable for irradiation of a first region of the tumor;
   c) irradiating the tumor;
   d) translating the collimator in a direction substantially transverse to said first radiation angle to scan the tumor;
   e) irradiating a further region of the tumor;
   f) repeating steps d) and e) until a desired region of the tumor is irradiated with the first aperture size;
   g) setting a further aperture opening of the collimator which differs from the first aperture opening;
   h) repeating steps d) through g) until a desired region of the tumor is irradiated;
   i) positioning the iris diaphragm collimator to irradiate the tumor from a second irradiation angle which differs from the first irradiation angle; and
   j) repeating steps b) through i) until a desired dose of radiation has been applied to the tumor.

2. The method of claim 1, wherein the first aperture opening is larger than the further aperture opening.

3. The method of claim 1, wherein one diaphragm leaf remains stationary during at least one of steps b) and g).

4. The method of claim 3, wherein the first aperture opening has a shape which differs from a shape of the further aperture opening.

5. A device for stereotactic, conformal radiation therapy of tumors, the device comprising:
   an iris diaphragm collimator having at least three diaphragm leaves, said diaphragm leaves defining a beam-limiting opening such that a sliding movement along side surfaces of said leaves takes place by a number of diaphragm leaves which is reduced by at most one;
   a mechanism for positioning said iris diaphragm collimator to irradiate the tumor from an irradiation angle;
   a mechanism for setting an aperture opening of said iris diaphragm collimator suitable for irradiation of a first portion of the tumor;
   a mechanism for irradiating the tumor; and
   a scanning mechanism for translating said iris diaphragm collimator in a direction substantially transverse to said irradiation angle with said irradiation angle and said aperture opening thereby remaining substantially unchanged, thereby permitting irradiation of a second portion of the tumor which differs from the first portion of the tumor.

6. The device of claim 5, wherein said setting mechanism does not induce displacement of one diaphragm leaf.

7. The device of claim 6, wherein said setting mechanism generates aperture openings of differing shapes.

8. The device of claim 5, wherein said diaphragm leaves have touching side surfaces enclosing a same angle.

9. The device of claim 5, wherein the device comprises a robot arm on which a radiation source and said iris diaphragm collimator are disposed, said robot arm comprising both said positioning mechanism and said scanning mechanism.

10. The device of claim 5, wherein a gantry brings a radiation source and said iris diaphragm collimator into various solid angle alignments of radiation, limited by the iris diaphragm collimator, relative to an object being treated, said gantry comprising said positioning mechanism.

11. The device of claim 5, wherein said iris diaphragm collimator has a shielding capability designed for high-energy radiation from a radiation source in a megavolt range.

12. The device of claim 11, wherein said diaphragm leaves have a thickness between 6 and 10 cm.

13. The device of claim 8, wherein a sliding movement of all diaphragm leaves is effected by equal adjustment paths, so that, after positioning, said opening is formed by sub-regions of said side surfaces that have an equal distance from a center.

14. The device of claim 8, wherein said diaphragm leaves are supported by linear guides running in a direction of sliding movement.

15. The device of claim 5, wherein said iris diaphragm collimator has four diaphragm leaves.

16. The device of claim 15, wherein each side surface forming said opening transitions at an inner end thereof into a tab-like, projecting circular arc forming a quarter circle, so that said four diaphragm leaves can selectively form a round opening or square openings, with rounded corners, of various sizes.

17. The device of claim 5, wherein said iris diaphragm collimator has at least six diaphragm leaves.

18. The device of claim 5, further comprising loading devices that press said side surfaces of said diaphragm leaves against each other.

19. The device of claim 18, wherein said loading devices comprise springs which act on said diaphragm leaves.

20. The device of claim 18, wherein said side surfaces have common guides with side surfaces of adjacent diaphragm leaves being shifted relative to each other in adjacent regions thereof not used for forming said opening.

21. The device of claim 5, wherein sliding movement of said diaphragm leaves is realized such that at least one diaphragm leaf is driven.

22. The device of claim 21, wherein all of the diaphragm leaves are simultaneously driven.

23. The device of claim 22, wherein a drive is provided for each diaphragm leaf with simultaneous movement being realized by an electronic controller.

24. The device of claim 22, wherein one drive simultaneously drives all of diaphragm leaves via a mechanism.

25. The device of claim 24, wherein said mechanism drives diaphragm leaves by means of adjusting cams arranged in a spiral on a cam disk that rotates about a center.

26. The device of claim 24, wherein said mechanism has a regulating element that can rotate about a center to act on each diaphragm leaf via a regulating arm.

27. The device of claim 26, further comprising restoring springs acting against said sliding movement via said regulating arm.

28. The device of claim 5, wherein touching side surfaces of said diaphragm leaves define tolerance dependent gaps which are not parallel to a beam path.

29. The device of claim 28, wherein said side surfaces have non-planar structures which engage in complementary fashion in a sliding direction.

30. The device of claim 28, wherein said iris diaphragm collimator is tilted relative to an imaginary diaphragm plane lying perpendicular to an optical axis, such that a beam can no longer pass through said gaps.

31. The device of claim 5, further comprising a fixed diaphragm for additional shielding located in a beam path outside of said iris diaphragm collimator, said fixed diaphragm having an opening which is adjusted to a greatest possible opening of said iris diaphragm collimator.

32. A device for stereotactic, conformal radiation therapy of tumors, the device comprising:

means for positioning an iris diaphragm collimator to irradiate the tumor from a first irradiation angle, the iris diaphragm having at least three diaphragm leaves, wherein the diaphragm leaves open up a beam-limiting opening such that a sliding movement along side surfaces of the diaphragm leaves takes place by a number of diaphragm leaves which is reduced by at most one;

means for setting a first aperture opening of the collimator suitable for irradiation of a first portion of the tumor at said first irradiation angle;

means for irradiating the first portion of the tumor at said first irradiation angle;

means for translating the collimator in a direction substantially transverse to said first irradiation angle to scan a second portion of the tumor at said first irradiation angle using said first aperture opening, wherein the second portion of the tumor differs from the first portion of the tumor;

means for irradiating the second portion of the tumor;

means for a setting a second aperture opening of the collimator which differs from the first aperture opening;

means for irradiating a third portion of the tumor using the second aperture opening, wherein the third portion of the tumor differs from both the first and second portions of the tumor; and means for positioning the iris diaphragm collimator to irradiate the tumor from a second irradiation angle which differs from the first irradiation angle.

* * * * *